United States Patent
Chan et al.

(10) Patent No.: US 7,824,469 B2
(45) Date of Patent: Nov. 2, 2010

(54) METHOD AND APPARATUS FOR FLUID PURIFICATION

(75) Inventors: Yiu Wai Chan, Hong Kong (HK); Sui Chun Law, Hong Kong (HK)

(73) Assignee: Akos Advanced Technology Ltd., Shatin, N.T. (HK)

( * ) Notice: Subject to any disclaimer, the term of this patent is extended or adjusted under 35 U.S.C. 154(b) by 269 days.

(21) Appl. No.: 12/106,504

(22) Filed: Apr. 21, 2008

(65) Prior Publication Data

US 2008/0314243 A1 Dec. 25, 2008

(30) Foreign Application Priority Data

Apr. 19, 2007 (EP) .................................. 07106505

(51) Int. Cl.
*B03C 3/38* (2006.01)
(52) U.S. Cl. ..................... 95/28; 95/90; 96/16; 96/224; 204/157.15; 204/157.3; 204/158.2; 204/158.21; 250/492.1; 250/492.2; 250/492.3; 250/423 R; 250/432 R
(58) Field of Classification Search ...... 95/28, 95/90; 96/16, 224; 204/157.15, 157.3, 158.2, 204/158.21; 250/492.1–492.3, 423 R–423 F, 250/432 R–438
See application file for complete search history.

(56) References Cited

U.S. PATENT DOCUMENTS

| 5,874,701 A * | 2/1999 | Watanabe et al. ...... 204/157.15 |
| 5,919,422 A * | 7/1999 | Yamanaka et al. ......... 422/121 |
| 6,624,584 B2 * | 9/2003 | Schmidt-Boecking et al. ... 315/111.81 |
| 2003/0000824 A1 | 1/2003 | Taoda et al. |
| 2006/0182670 A1 | 8/2006 | Allen |

FOREIGN PATENT DOCUMENTS

WO    WO/95/23517    9/1995

* cited by examiner

*Primary Examiner*—Robert J Hill, Jr.
*Assistant Examiner*—Christopher P Jones
(74) *Attorney, Agent, or Firm*—Kauth, Pomeroy, Peck & Bailey LLP (57) ABSTRACT

A catalytic system (10) for fluid purification, the system (10) comprising: at least one photon source (2) to substantially break down at least two types of target molecules in the fluid to create short lived intermediates; and a ceramic core (5) including at least one type of micropore to adsorb the short lived intermediates for the propagation reactions and termination reactions of the short lived intermediates.

19 Claims, 9 Drawing Sheets

METHOD AND APPARATUS FOR FLUID PURIFICATION

CROSS-REFERENCE TO RELATED APPLICATIONS

The current application claims priority to European Patent Application No. 07 106 505.6 filed Apr. 19, 2007, the disclosure of which is incorporated herein by reference.

FIELD OF THE INVENTION

The invention concerns a method and apparatus for fluid purification, by increasing fluid flow rates and efficiency. In particular, the invention concerns air purification systems which have a filter core that is continuously self-regenerating that permanently removes target molecules.

BACKGROUND OF THE INVENTION

Air purification traditionally involved the use of a HEPA filter, ionizer, or electrostatic precipitator to remove particulate matter and airborne bacteria from the air. To reduce gas-phase pollutants, adsorbent materials including activated carbons and molecular sieves may be used. Adsorption is only effective at the early stage and efficiency is gradually reduced because of the eventual saturation of the adsorbent materials. Using adsorbent materials is not environmental friendly because it requires frequently replacement and merely transfers gas-phase pollutants into particle-phase pollutants.

Ozone generators for oxidation of gases pollutants may be used. Low level ozone generated by the ozone generators is ineffective for air purification, while high level ozone is harmful to human beings. The atmospheric lifetime of tropospheric ozone is about twenty two days. To reduce the lifespan of ozone, ozone or an oxidation reagent is combined with an adsorbent. The adsorbent acts as a confined media for the reaction to take place.

CN 1625675A discloses the use of an oxidizing agent and zeolite. The pollutant first passes through an oxidizing generator before entry into a molecular sieve housing the molecules. The purification process is ineffective because oxidation of the pollutant is too slow in a confined space such as the nanopores/micropores of zeolite and molecular sieve even if it contains an active site for a reaction. This is because when the reactant enters the pores, it is at its lowest energy level stage. In other words, the reactant is too stable to start and initiate any reaction. Furthermore, the pore volume of the zeolite and molecular sieve are a constant size throughout the entire reaction. Therefore smaller sized harmful intermediates are not held longer in the pore and are released to the environment in the middle of the reaction.

U.S. Pat. No. 5,835,840 discloses a method of air purification using photo catalytic oxidation on a surface of titanium oxides. A catalyst such as titanium dioxide is fixed on a matrix or on the surface of a duct such that ultraviolet light is incident on the catalyst as air moves over it. However, photo catalytic oxidation of a pollutant over a surface is too slow and not feasible for high air flow. High air flow may be achieved by using a long air duct with an ultraviolet irradiation system and controlling the rate of air flow. The system design is limited because it requires direct irradiation by the ultraviolet irradiation system onto the surface of the catalyst. Using a long air duct for the ultraviolet irradiation system increases the bulkiness of the system and does not permit a compact design. The system is unable to handle high level contaminant gases.

SUMMARY OF THE INVENTION

In a first preferred aspect, there is provided a catalytic system for fluid purification, the system including:
  at least one photon source to substantially break down at least two types of target molecules in the fluid to create short lived intermediates; and
  a ceramic core including at least one type of micropore to adsorb the short lived intermediates for propagation reactions and termination reactions of the short lived intermediates.

The micropore may include a nanopore.

The system may further include at least one charged ion generator for generating charged ions in the fluid, the at least one charged ion generator being positioned upstream from the ceramic core.

The generated charged ions may occupy a specific space and are able to alter the space volume of the ceramic core at the same time when exchanged with the charged ions previously residing in the micropores of the ceramic core.

The ceramic core may be a charged framework and is charged balanced by including at least one type of cation, at least one type of anion, or a mixture of cation and anion, in the micropores of the ceramic core.

The space volume of the micropores may be altered at substantially the same time to house the short lived intermediates during the propagation reaction and until the termination reaction.

The nanopores of the ceramic core may be arranged in a channel formation, the channel formation being formed according to any one from the group including: one, two or three dimensional and the combination thereof.

The ceramic core may be made from materials including any from the group including: oxides, non oxides, or the composites of particulate reinforced from oxides and non-oxides, or the mixtures of thereof.

All the target molecules may be in a homogenous phase.

If the system is used in an air purifier system, at least one of the target molecules may be a volatile organic compound from any one of the functional group including: alkane, alkene, alkynes, halogens, aldehyde, ketones, carboxylic acid, ethers, ester, amine, amides, alcohols, cyclic, and the mixtures thereof, and the target molecules are able to be photodissociated into carbon reactive intermediates upon irradiation by the at least one photon source.

The carbon reactive intermediates may be any one from the group including: carbocations, carboanions and free radicals.

If the system is used in an air purifier system, at least one of the target molecules may be an oxidant, and upon irradiation by the at least one photon source, the target molecules are able to be changed to short lived intermediate with a lifespan comparable to the carbon reactive intermediates.

The oxidant may be any from the group including: oxygen molecule, ozone molecule, and any anion of ozone including $O_4$, $O_5$, $O_6$, $O_7$ generated by methods of corona discharge, cold plasma and UV irradiation, and upon irradiation by the at least one photon source, the target molecules are able to be photodissociated into an excited singlet oxygen atom and oxygen molecules.

The oxidant may be a water molecule from the ambient environment, and upon irradiation by the at least one photon source, the target molecules is able be photodissociated into hydroxyl radicals.

The at least one photon source may emit electromagnetic waves in a range from visible light to gamma ray region, and with a wavelength less than 350 nm.

The system may further include a dual functioning device to generate oxidant as part of the target molecules and emit electromagnetic waves in a range from visible light to gamma ray region at wavelength less than 300 nm.

The system may further include an electronic control device for intelligently controlling the intensity of the at least one photon source, movement speed of the target molecules, and capacity of the at least one charged ion generator according to the amount of target molecules to be treated.

In a second aspect, there is provided a method for fluid purification, the method including:

substantially breaking down at least two types of target molecules in the fluid to create short lived intermediates;

receiving the short lived intermediates; and processing the propagation reactions and termination reactions of the short lived intermediates.

The at least two types of target molecules may be substantially broken down by at least one photon source.

The short lived intermediates may be received in a ceramic core including at least one type of micropore.

The present invention aims to increase the rate of reaction by causing the reactant to be in an excited and unstable state when it enters porous materials.

The present invention also prevents the leakage of harmful short lived intermediates into the environment by having pores that prevent the passage of large sized intermediates. As most short lived intermediates are very reactive and decay very quickly when they contact molecules in the ambient air, the housing of the short lived intermediates within a confined space volume ensures the reaction is carried out and propagated until the simplest non-reactive species are formed.

In contrast to a traditional photocatalytic system, the present invention does not require the photon source to directly irradiate the surface of catalytic core. The present invention enables a high degree of design freedom for the system.

As the propagation reactions are carried out within the nanopores/micropores of the ceramic core rather than on the surface of catalyst, the rate of reaction is faster. The increase in effectiveness eventually leads to a system size reduction, which enables the present invention to be used for compact air purification systems.

BRIEF DESCRIPTION OF THE DRAWINGS

Examples of the invention will now be described with reference to the accompanying drawings, in which.

DETAILED DESCRIPTION OF THE DRAWINGS

Figure 1:
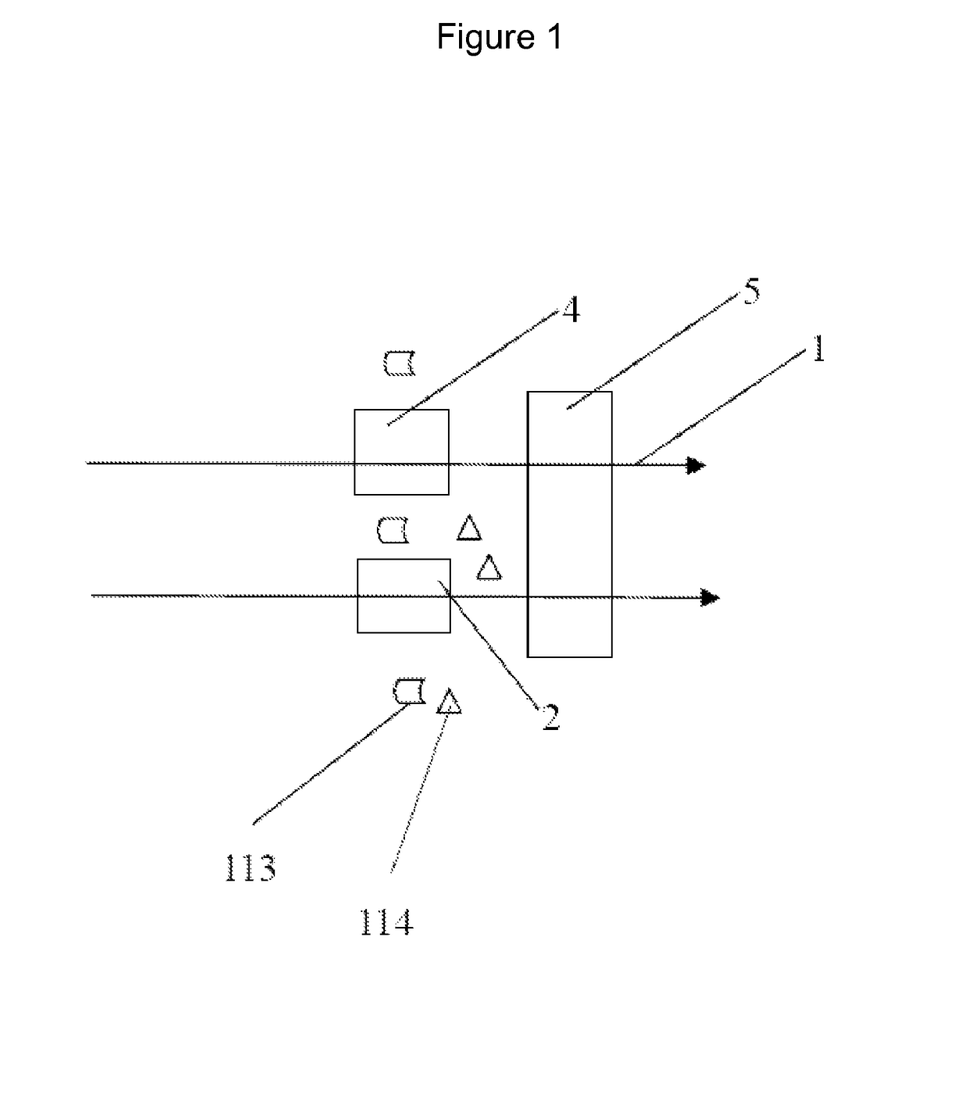
FIG. 1 is a schematic diagram of the present invention according to a first embodiment.

Referring to FIG. 1, a catalytic system 10 for enhancing fluid purification is provided. The system 10 generally comprises: at least one photon source 2 and a ceramic core 5. The photon source 2 substantially breaks down at least two types of target molecules in the fluid into short lived intermediates. The ceramic core/filter 5 includes at least one type of micropore to adsorb the short lived intermediates 114 for the propagation reactions and termination reactions of the short lived intermediates 114. The termination reactions produce the simplest non-reactive molecule in comparison to the original target molecules and short lived intermediates, and therefore purify the fluid.

Figure 9:
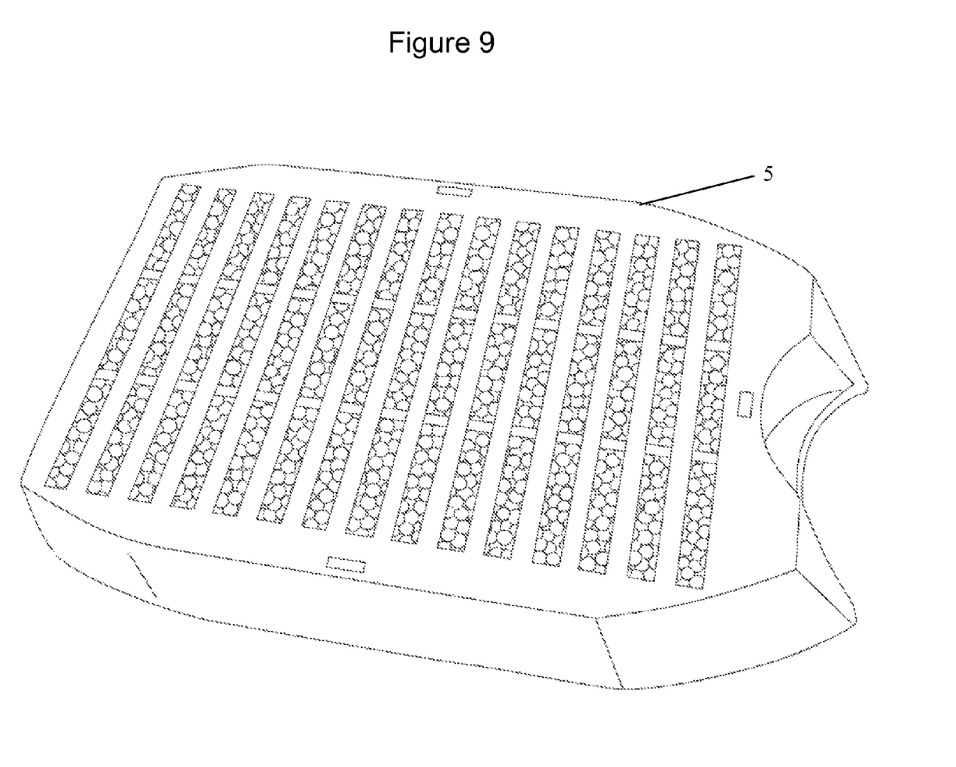
FIG. 9 is a planar view of a ceramic core in accordance with a preferred embodiment of the present invention.

Turning to FIG. 9, the ceramic core 5 may be made from materials including oxides, non oxides, or the composites of particulate reinforced from oxides and non-oxides, or the mixtures of thereof. The pores of the ceramic core 5 may also contain active sites for accelerating the propagation reaction. Using oxide materials favors the formation of H-bonding with the hydrophilic functional groups of the short lived intermediates and ensures they are securely held in the pores. Using non-oxide materials favors the attraction of hydrophobic functions group of the short lived intermediates.

The photon source 2 emits electromagnetic waves in the range from visible light to the gamma ray region, and has a wavelength less than 350 nm. The oxidant generating device 4 generates an oxidizing agent, such as ozone or hydroxyl radicals. The air stream 1 is forced to flow through the photon source 2 and the oxidant generating device 4. The generated oxidant is irradiated by the photon source 2 to generate the short lived intermediates, target carbon reactive intermediates 113 and short lived intermediates of the oxidant 114. The air stream 1 is mixed together and forced through the ceramic core 5 where the short lived intermediates are adsorbed for further propagation reaction and termination reaction.

If the photon source 2 emits a shorter wavelength, the intensity is higher and is more effective in generating the short lived intermediates. The distance of the photon source 2 and the ceramic core 5 is such that newly formed short lived intermediates are adsorbed into the pores of the ceramic core 5 before decaying in the air. The relationship between the distance (D) of the photon source 2 and the ceramic core 5, the intensity (I) and wavelength ($\lambda$) in the system 10 with a system constant (C) is determined according to the following equation: $D=C/(I \times \lambda)$ Referring to FIG. 2, in another embodiment that is more efficient, a charged ion generator 3 for generating charged ions is provided. Charged ions such as positively charged cations 111 and negatively charged anions 112 are generated by the charged ion generator 3. The charged ion generator 3 is placed upstream from the photon source 2 and the oxidant generating device 4. The air stream 1 is forced to flow through or proximal to the charged ion generator 3, and then through or proximal to the oxidant generating device 4 and the photon source 2. The short lived intermediates, target carbon reactive intermediates 113 and the short lived intermediates of the oxidant 114 are generated when the target molecule in the air stream 1 passes over the photon source 2 and is irradiated. The air stream 1 mixes together and forced through the ceramic core 5 where the short lived intermediates are adsorbed for further propagation reaction and termination reaction.

Figure 2:
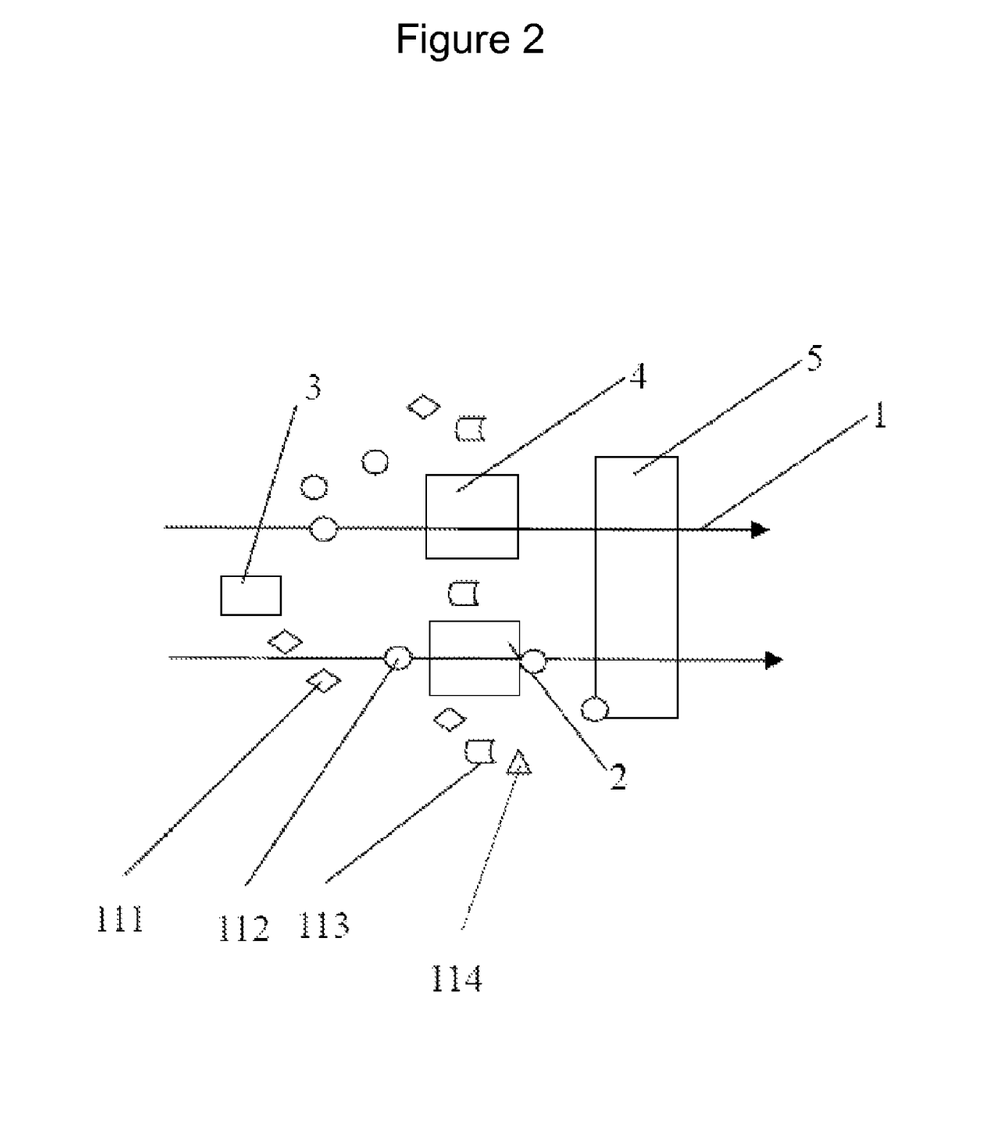
FIG. 2 is a schematic diagram of the present invention according to a second embodiment.

The pore volume of the ceramic core 5 may be altered at the same time and continuously throughout the propagation reaction. The charged ion generator 3 provides sufficient energy which is comparable or higher than the first ionization energy of the air stream 1, to ionize the gases and generate the charged ions. The magnitude of a charged ion may be measured by an ion counter. The cation and anion generated by the charged ion generator 3 are drawn into the nanopores/micropores of the ceramic core 5. The charged ions occupy a specific space and alter the space volume of the nanopores/micropores of the ceramic core 5 at the same time by exchanging position with the original charged cation and anion in the nanopores/micropores.

The space volume of the nanopores/micropores of the ceramic core 5 is able to be altered for fitting and housing the short lived intermediates formed during the propagation reaction. The short lived intermediates are held within the pores until they are broken down into the smallest size non-reactive species and prevented from being released to the environment or poisoning the catalyst. The propagation reaction of the intermediates is performed within the pores which are confined in space and the space volume may be altered during the process of the propagation reaction. At the end of the propagation reaction, the non-reactive molecules are formed and they vacate the pores of the ceramic core 5 for the next incoming propagation reaction. By allowing the pore volume to be altered at the same time and continuously throughout the propagation reaction, non-reactive simple molecules such as $H_2O$ and $CO_2$ are ultimately created. These non-reactive simple molecules are then released kinetically or thermally from the pore to the environment.

Figure 3:
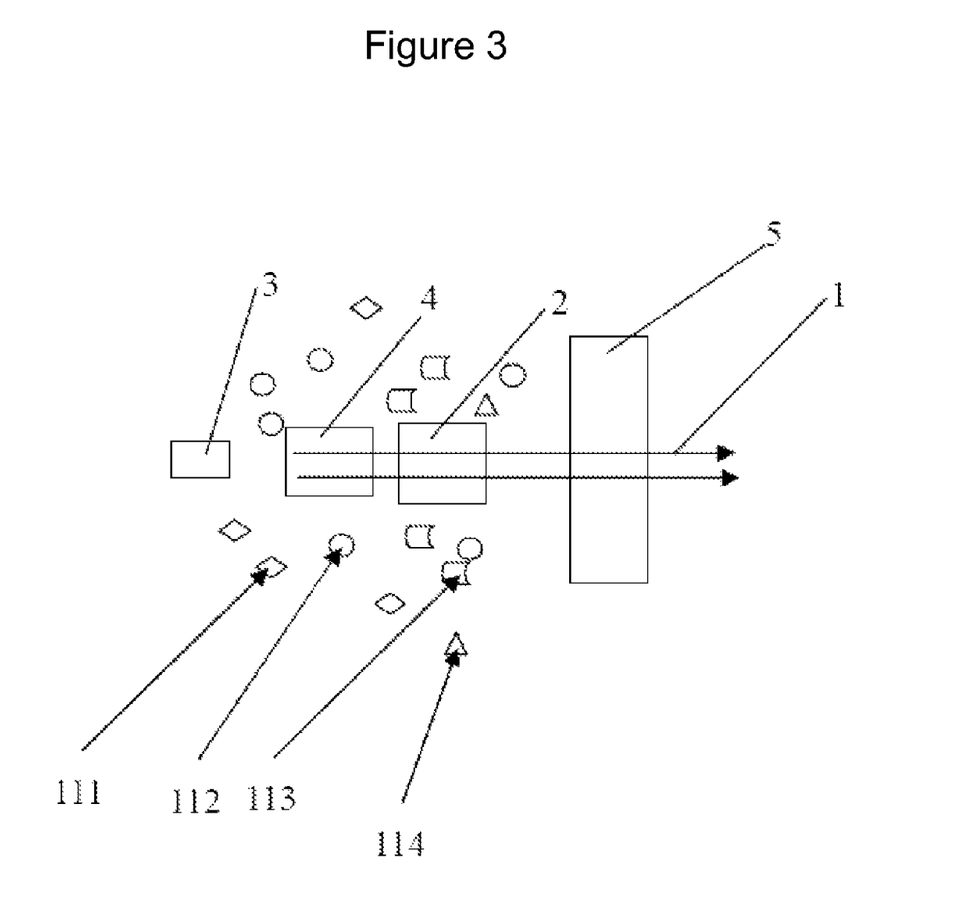
FIG. 3 is a schematic diagram of the present invention according to a third embodiment.

Referring to FIG. 3, in another embodiment, the charged ion generator 3 for generating cations 111 and anions 112 is placed upstream from the photon source 2 and oxidant generating device 4. Initially, the air stream 1 is forced to flow through the charged ion generator 3. Next, the air stream 1 is forced through the oxidant generating device 4. The oxidant 115 generated from the oxidant generating device 4 is then irradiated by the photon source 2, which generates the short lived intermediates of the oxidants 114 and target carbon reactive intermediates 113. Next, the air stream 1 is forced through the ceramic core 5 where the short lived intermediates are adsorbed for further propagation reaction and termination reaction.

Figure 4:
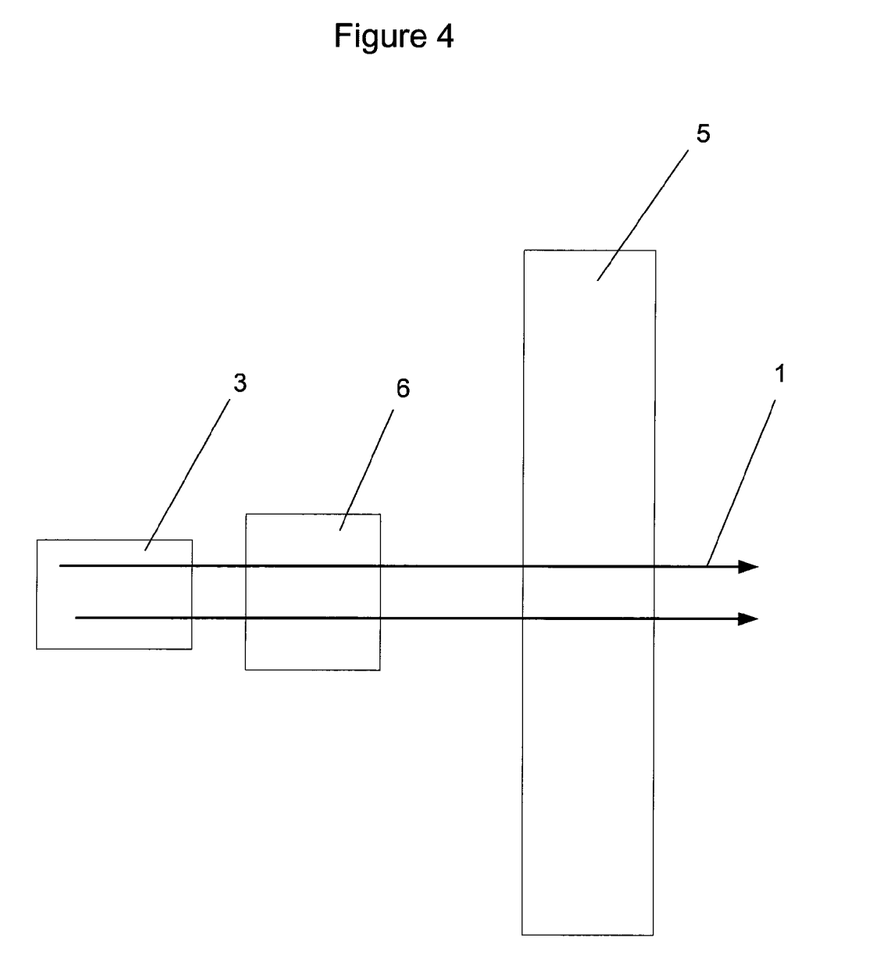
FIG. 4 is a schematic diagram of the present invention according to a fourth embodiment.

Referring to FIG. 4, in another embodiment, a dual function device 6 is provided. The dual function device 6 performs the functions of a photon source and an oxidant generating device. A charged ion generator 3 for generating cations 111 and anions 112 is placed upstream from the dual function device 6. Initially, the air stream 1 is forced to flow through or proximal to the charged ion generator 3. Next, the air stream 1 is then forced through the dual function device 6, where oxidant 115 is generated. The generated oxidant 115 is irradiated by the photon source of the dual function device 6. At the same time, short lived intermediates of the oxidants 114 and target carbon reactive intermediates 113 are generated. The air stream 1 is then forced through a ceramic core 5 where the short lived intermediates are adsorbed for further propagation reaction and termination reaction.

Figure 5:
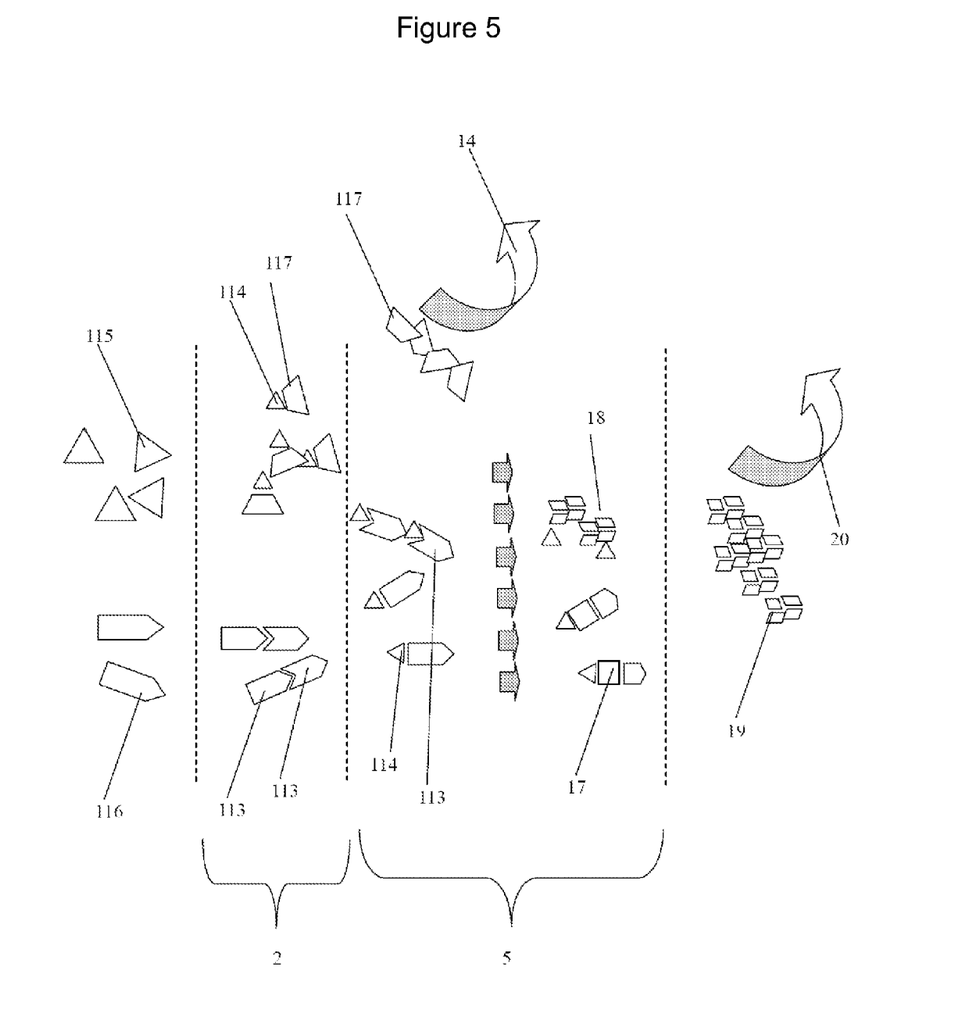
FIG. 5 is a working principle diagram of the present invention.

Referring to FIG. 5, a working principle diagram of the present invention is shown, from left to right. Initially, the oxidant 115 and the contaminant gases molecules 116 are broken down into target carbon reactive intermediates 113 and the short lived intermediates of the oxidants 114 upon irradiation by the photon source 2. Some stable non-target molecules 117 may be formed at this stage. The target carbon reactive intermediates 113 and the short lived intermediates of the oxidants 114 are then forced to enter the ceramic core 5. The stable non-target molecules 117 are not adsorbed by the ceramic core 5 and are released to the environment. Inside the pores of the ceramic core 5, the target carbon reactive intermediates 113 and the short lived intermediates of the oxidants 114 are self-rearranged according to the pore volume available and also undergo a propagation reaction. Smaller sized short lived intermediates 17, 18 are formed. At the end of the propagation reaction, only the simplest non-reactive species 19 are formed and released 20 to the environment.

Figure 6:
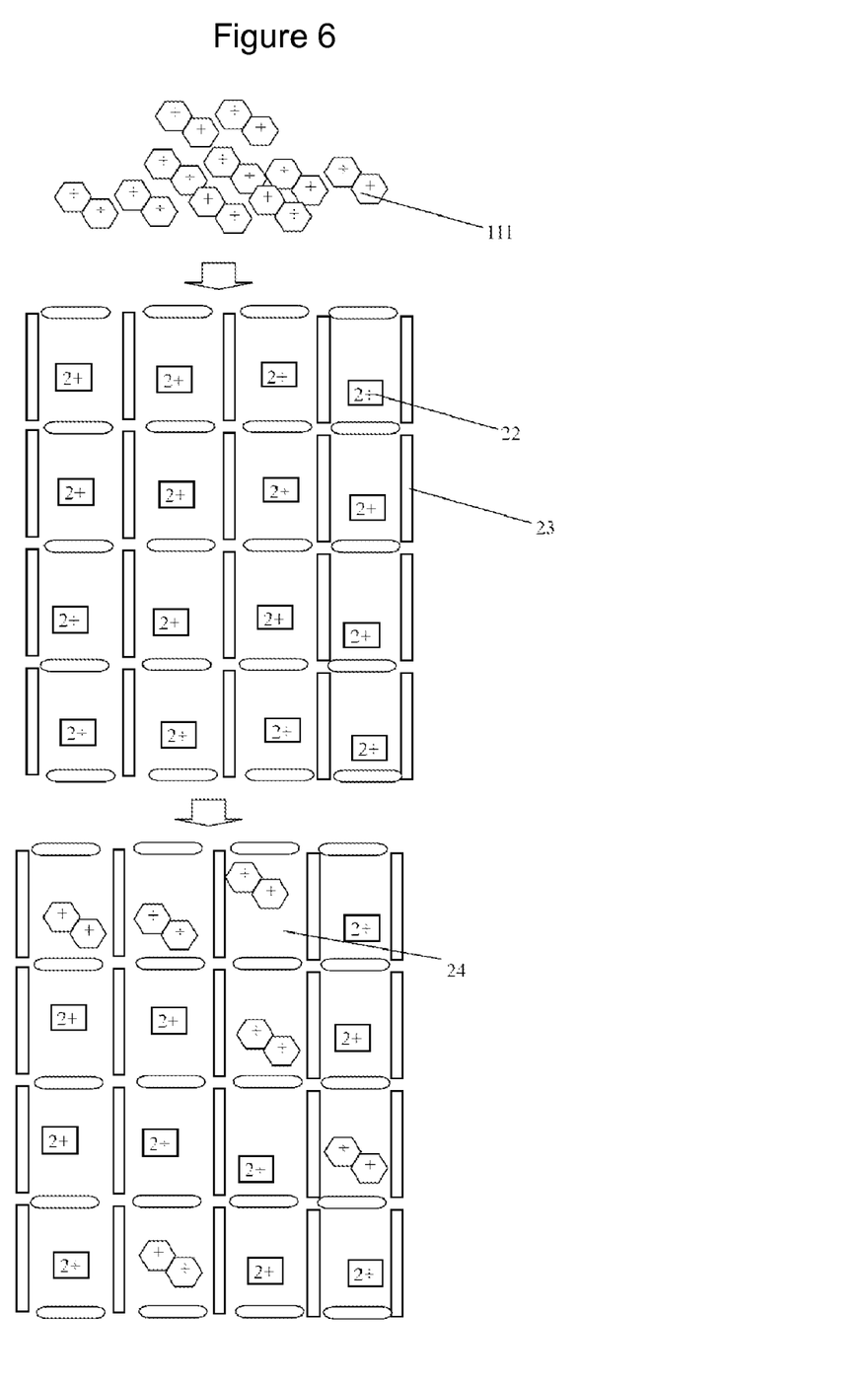
FIG. 6 is a pictorial diagram of the alternation of space volume of the nanopores/micropores of a ceramic core in accordance with a preferred embodiment of the present invention.

Referring to FIG. 6, a diagram of the alternation of space volume of the nanopores/micropores of the ceramic core 5 by the incoming specific space occupying cations 111 is shown. The cations 111 are generated by the charged ion generator 3 of FIGS. 2 and 3, and enter the ceramic core 5. Preferably, the ceramic core 5 is an anionic charged framework 23 charged balanced by some specific space occupying cations 22. At least some pore volume 24 is altered by the exchange of cations 111 with the original cations 22 in the ceramic core 5. Alternatively, the ceramic core 5 is a charged framework and is charged balanced by including at least one type of cation, or at least one type of anion, or a mixture of cation and anion in its nanopores/micropores. The charged framework 23 allows the attraction and housing of neutral and opposite charged ions, intermediates and fragments. A charged framework 23 is preferable to an uncharged framework because an uncharged framework does not have a special affinity to neutral intermediates and fragments. In a detrimental sense, an uncharged framework may even oppose charged ions, intermediates and fragments.

Figure 7:
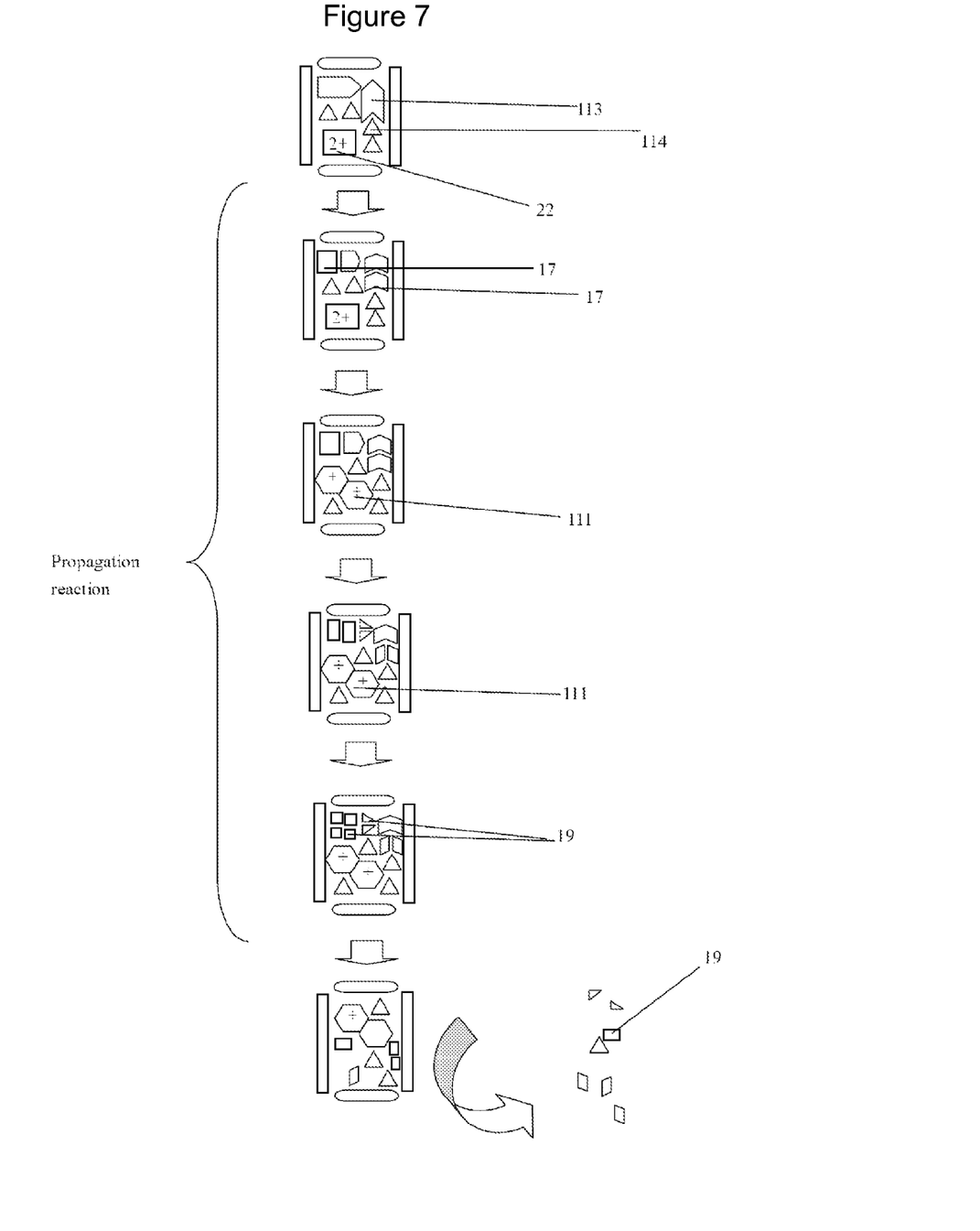
FIG. 7 is a pictorial diagram that indicates the propagation reaction in a space volume alternating nanopores/micropores of a ceramic core in accordance with a preferred embodiment of the present invention.

Referring to FIG. 7, a graphical depiction of the propagation reaction in the space volume alternating nanopores/micropores of the ceramic core 5, from top to bottom is shown. The target carbon reactive intermediates 113, short lived intermediates of the oxidants 114, and the original specific space occupying cations 22 are held in the pores of the ceramic core 5 illustrated in FIGS. 2 to 6. During the propagation reaction, smaller sized short lived intermediates 17 are formed. Incoming cations 111 with specific space volume occupying exchange position with the original cations 22 in the charged framework 23. The change of space volume allows better housing of the smaller sized short lived intermediates 17. When the non-reactive stable species are formed (which is simplest in molecular structures 19); they are released to the environment kinetically and thermally.

Figure 8:
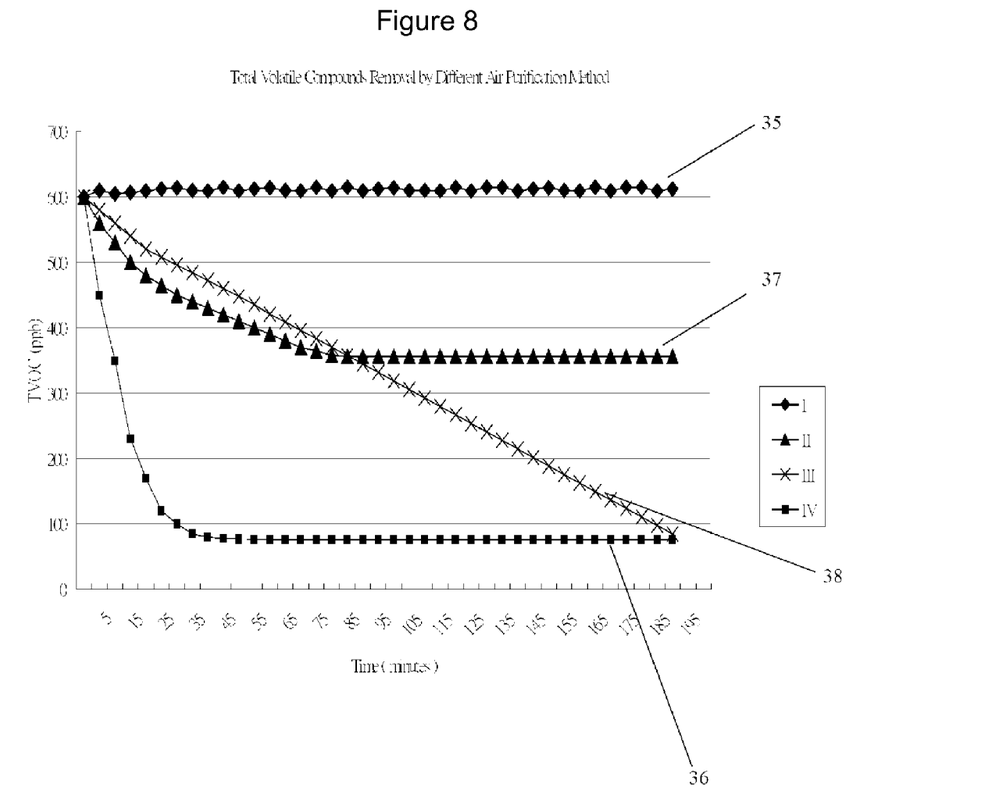
FIG. 8 is a chart comparing the performance of contaminant removal (I) without treatment (II), without a photon source, (III) with a single pore channel in the ceramic core, and (IV) with three dimensional pore channels in a ceramic core in accordance with a preferred embodiment of the present invention.

FIG. 8 shows a chart of the performance difference comparing: (I) without treatment (II) without a photon source 2, (III) a with a single pore channel in the ceramic core 5, and (IV) with a three-dimensional pore channel ceramic core 5. The comparison was performed in a controlled environment where different chemical species: a mixture of xylene, toluene, dichloroethane, acetone, and hexane and ethylene diether, were used as sources of contaminant gases, i.e. as a source of Total Volatile Organic Compounds (TVOC). Arranging the nanopores/micropores into channel structures in the ceramic core 5 ensures the non-reactive molecules are freely movable from one pore to another and may move out to the environment to vacate its pore for the next propagation reaction. Using a ceramic core 5 with a larger dimension for a nanopores/micropores channel is preferable. This ensures that even when one of the dimensions of the pore channel is blocked during a propagation reaction, the other dimensions of the pore channel are available for the movement of the non-reactive molecule.

Curve 35 illustrates that the TVOC level remained unchanged if no air treatment using any of the embodiments of the present invention was used. If the system 10 is used as an air purifier without a photon source, the TVOC level is reduced to only certain level, as shown by Curve 37. If a single dimensional nature for the pore channels is used in the ceramic core instead of a higher dimension of pore channels, it may take a longer time for the pollutants to be reduced to its lowest level as shown by Curve 38. However, if a three dimensional nature for the pore channels is used in the ceramic core, the TVOC level may be reduced to its lowest level relatively quickly, as shown by Curve 36.

The catalytic system 10 may be incorporated into an apparatus for fluid purification. The apparatus comprises a housing having at least one inlet and an outlet for fluid communication, at least one photon irradiation device, a ceramic core, and a fluid circulating device. The photon irradiation devices, ceramic core and circulating device are installed inside the housing. The photon irradiation device is located upstream from the ceramic core. The circulating device causes the fluid to flow from upstream to downstream. During operation of the apparatus, at least two types of target molecules are broken down into short lived intermediates separately by the at least one irradiation device. The short lived intermediates are then received by the ceramic core which includes at least one type of nanopores/micropores. The propagation reactions and termination reactions of the short lived intermediates are processed in the ceramic core.

The catalytic system 10 may be used with any air treatment device, such as an air conditioner, vacuum cleaner, ventilation unit, humidifier, dehumidifier, heater, electrostatic precipitator, or particulate filter. The catalytic system 10 may be integrated with an electronic control device for intelligently controlling the intensity of the photon source, movement speed of the target molecules, and capacity of the charged ion generator according to the amount of target molecules to be treated.

Air Purification System

If the catalytic system 10 is used in an air purification system, the target molecules are in a homogenous phase as follows:

(a) at least one of the target molecules is a volatile organic compound which contains one from the functional group including: alkane, alkene, alkynes, halogens, aldehyde, ketones, carboxylic acid, ethers, ester, amine, amides, alcohols, cyclic, or the mixtures of the thereof. The target molecule is able to be photodissociated into carbon reactive intermediates upon irradiation by a photon source. The carbon reactive intermediates include any species of carbocations, carboanions and free radicals.

(b) at least one of the target molecules is an oxidant. Upon irradiation by a photon source, the oxidant is able to be photodissociated into short lived intermediates with a lifespan in the same order of magnitude to carbon reactive intermediates. The reaction between the short lived intermediates of the oxidant and the carbon reactive intermediates become kinetically favorable.

The oxidant may include oxygen molecules, ozone molecules, or any of the anions of ozone which include $O_4$, $O_5$, $O_6$, $O_7$ generated by methods of corona discharge, cold plasma or UV irradiation. Upon irradiation of the photon sources, the target molecules are photodissociated into an excited singlet oxygen atom and oxygen molecules. The excited singlet oxygen atom is a short lived intermediate and it is much more reactive compared to the original tri-atom ozone molecules or oxygen molecule.

The oxidant may be water molecules from the ambient environment. Upon irradiation of by a photon source, the target molecules are photodissociated into hydroxyl radicals. Relative humidity is maintained at a level of at least 20% for generating of the hydroxyl radicals.

It will be appreciated by persons skilled in the art that numerous variations and/or modifications may be made to the invention as shown in the specific embodiments without departing from the scope or spirit of the invention as broadly described. The present embodiments are, therefore, to be considered in all respects illustrative and not restrictive.

What is claimed is:

1. A catalytic system for fluid purification, the system comprising:
    at least one photon source to substantially break down at least two types of target molecules in the fluid to create short lived intermediates; and
    a ceramic core including at least one type of micropore to adsorb the short lived intermediates for the propagation reactions and termination reactions of the short lived intermediates;
    at least one charged ion generator for generating charged ions in the fluid, the at least one charged ion generator being positioned upstream from the ceramic core;
    an oxidant generating device for generating an oxidizing agent, wherein the oxidant generating device is positioned upstream from the ceramic core;
    wherein the photon source is positioned upstream from the ceramic core and the photon source is configured to break down the at least two types of target molecules at a rate which allows the short lived intermediates to remain in an excited and unstable state when they enter the micropores of the ceramic core after traveling the space between the photon source and the ceramic core.

2. The system according to claim 1, wherein the micropore includes a nanopore.

3. The system according to claim 2, wherein the nanopores of the ceramic core are arranged in a channel. formation, the channel. formation being formed according to any one from the group consisting of: one, two or three dimensional and the combination thereof.

4. The system according to claim 1, wherein the generated charged ions occupy a specific space and are able to after the space volume of the ceramic core at the same time when exchanged with the charged ions previously residing in the micropores of the ceramic core.

5. The system according to claim 1, wherein the ceramic core is a charged framework and is charged balanced by including at least one type of cation, at least one type of anion, or a mixture of cation and anion, in the micropores of the ceramic core.

6. The system according to claim 1, wherein the space volume of the micropores are altered at substantially the same time to house the short lived intermediates during the propagation reaction and until the termination reaction.

7. The system according to claim 1, wherein the ceramic core is made from materials including any from the group consisting of: oxides, non oxides, or the composites of particulate reinforced from oxides and non-oxides, or the mixtures of thereof.

8. The system according to claim 1, wherein all the target molecules are in a homogenous phase.

9. The system according to claim 1, wherein if the system is used in an air purifier system, at least one of the target molecules is a volatile organic compound from any one of the functional. group consisting of: alkane, alkene, alkynes, halogens, aldehyde, ketones, carboxylic acid, ethers, ester, amine, amides, alcohols, cyclic, and the mixtures thereof, and the target molecules are able to be photodissociated into carbon reactive intermediates upon irradiation by the at least one photon source.

10. The system according to claim 9, wherein the carbon reactive intermediates is any one from the group consisting of: carbocations, carboanions and free radicals.

11. The system according to claim 10 wherein if the system. is used in an air purifier system, at least one of the target molecules is an oxidant, and upon irradiation by the at least one photon source, the target molecules are able to be changed to short lived intermediate with a lifespan comparable to the carbon reactive intermediates.

12. The system according to claim 9, wherein if the system is used in an air purifier system, at least one of the target molecules is an oxidant, and upon irradiation by the at least one photon source, the target molecules are able to be changed to short lived intermediate with a lifespan comparable to the carbon reactive intermediates.

13. The system according to claim 12, wherein the oxidant is any from the group consisting of: oxygen molecule, ozone molecule, and any anion of ozone including $O_4$, $O_5$, $O_6$, $O_7$ generated by methods of corona discharge, cold plasma and UV irradiation, and upon irradiation by the at least one photon source, the target molecules are able to be photodissociated into an excited singlet oxygen atom and oxygen molecules.

14. The system according to claim 12, wherein the oxidant is a water molecule from the ambient environment, and upon irradiation by the at least one photon source, the target molecules is able be photodissociated into hydroxyl radicals.

15. The system according to claim 1, wherein the at least one photon source emits electromagnetic waves in a range from visible light to gamma ray region, and with a wavelength less than 350 nm.

16. The system according to claim 1, wherein the oxidant generating device and the photon source comprises a dual. functioning device to generate oxidant as part of the target molecules and emit electromagnetic waves in a range from visible light to gamma ray region at wavelength less than 300 nm.

17. The system according to claim 1, further comprising an electronic control device for intelligently controlling the intensity of the at least one photon source, movement speed of the target molecules, and capacity of the at least one charged ion generator according to the amount of target molecules to be treated.

18. A method for fluid purification, the method comprising:
substantially breaking down at least two types of target molecules in the fluid to create short lived intermediates by at least one photon source;
adsorbing the short lived intermediates for the propagation reactions and termination reactions of the short lived intermediates in a ceramic core;
positioning the photon source, at least one charged ion generator and an oxidant generating device upstream from the ceramic core; and
configuring the photon source to break down the at least two types of target molecules at a rate which allows the short lived intermediates to remain in an excited and unstable state when they enter the micropores of the ceramic core after traveling the space between the photon source and the ceramic core, the charged ion generator to generate charged ions in the fluid by positioned upstream from the ceramic core, and the oxidant generating device to generate an oxidizing agent.

19. The method according to claim 18, wherein the ceramic core includes at least one type of micropore.

* * * * *